United States Patent [19]
Root

[11] Patent Number: 5,876,362
[45] Date of Patent: Mar. 2, 1999

[54] OMNIDIRECTIONAL ARM AND WRIST SUPPORT

[76] Inventor: Warren N. Root, 24921 Muirlands, Unit 112, Lake Forest, Calif. 92630

[21] Appl. No.: 42,516

[22] Filed: Mar. 16, 1998

[51] Int. Cl.[6] .............................. A61F 5/00; B41J 29/00
[52] U.S. Cl. .............................. 602/21; 400/715; 84/469
[58] Field of Search .............................. 601/40; 602/20, 602/21; 400/715; 84/328, 465, 467–469

[56] References Cited

U.S. PATENT DOCUMENTS

| | | | |
|---|---|---|---|
| 591,800 | 10/1897 | Finnblade et al. | 84/468 |
| 679,288 | 7/1901 | Bohrer | 84/468 |
| 3,782,719 | 1/1974 | Kuhlman | 84/468 X |
| 5,082,258 | 1/1992 | Niks | 84/467 X |

*Primary Examiner*—Linda C. M. Dvorak
*Attorney, Agent, or Firm*—Knobbe, Martens, Olson & Bear, LLP

[57] ABSTRACT

A support system for a user of a computer keyboard or for a person performing other manual tasks of extended duration includes a pair of supports which are positioned proximate to respective ends of the keyboard. A rod is supported between the pair of supports to provide a horizontal guide rail. Two pairs of rollers roll along the upper portion of the rod to provide a pair of trolleys from which are suspended a pair of independently moveable wrist cradles. When the user places his or her wrists in the cradles, the hands and lower arms are supported above the keyboard or other work surface so that the user is assisted in supporting the weight of his or her arms and hands. The cradles can be moved horizontally from left to right and vice versa as well as arcuately as the user's hands are moved closer to and farther from the user's body. Thus, the user is able to move his or her hands freely over the computer keyboard or other work surface even if the user does not have sufficient muscle tone to adequately support his or her arms for extended duration.

14 Claims, 4 Drawing Sheets

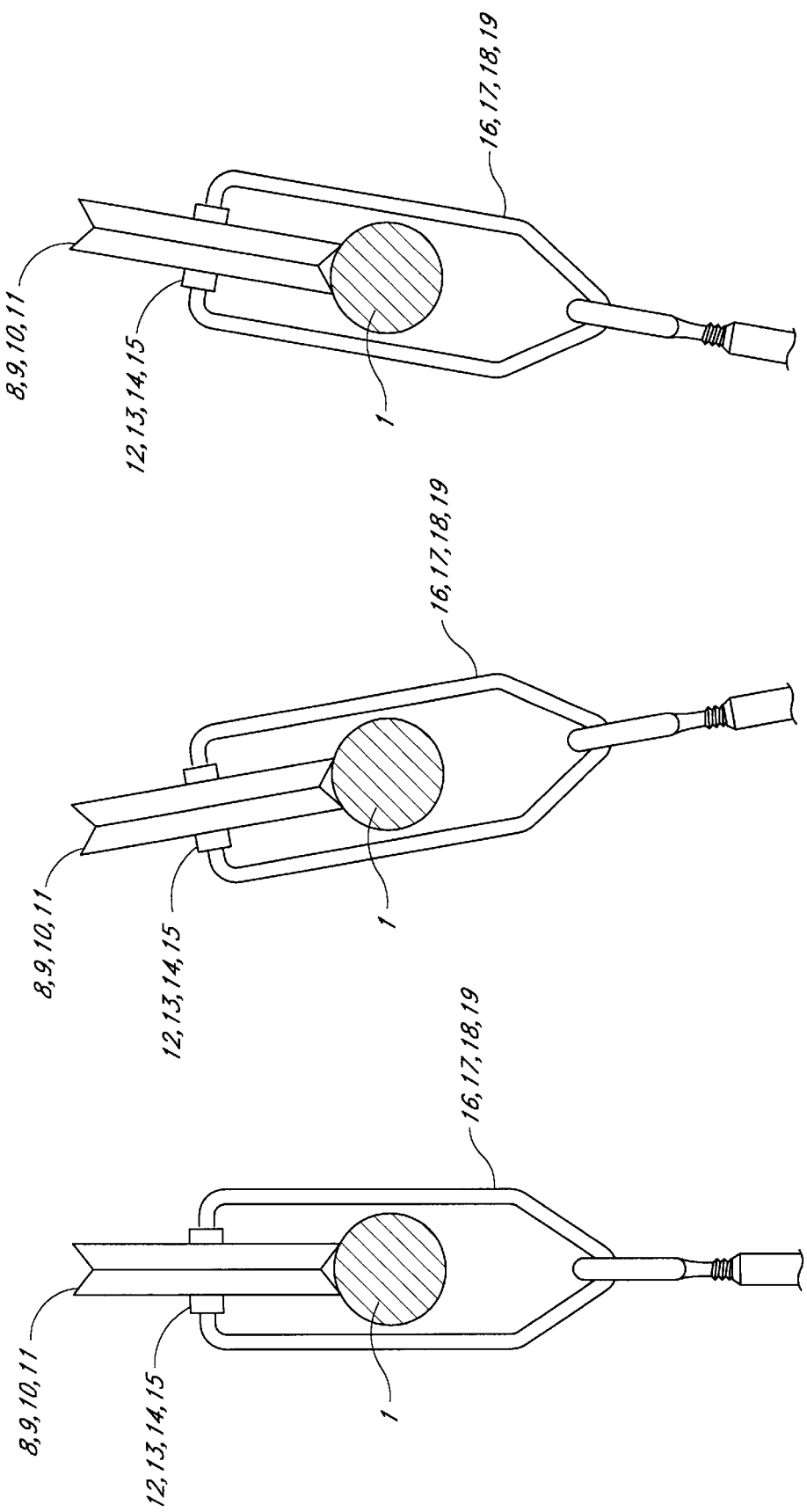

OMNIDIRECTIONAL ARM AND WRIST SUPPORT

FIELD OF THE INVENTION

The present invention is in the field of devices which support the lower arm and wrists during the performance of repetitive tasks such as typing, data entry, or the like.

DESCRIPTION OF THE RELATED ART

Many personal and job-related tasks involve the use of computer keyboards, calculators and other data entry devices which require a person to have his or her arms and hands extended in front of the person's body for long durations. In addition, other tasks, such as sewing, needlework, knitting, painting, or the like, require the arms and hands to be likewise extended. As a result of repeated periods of arm and hand extension, many persons have developed injuries such as carpal tunnel syndrome. In addition, because of aging, accidents, or certain diseases, some persons no longer have the ability to perform relatively simple tasks which require arm and hand extension. A number of devices have been developed to reduce the effects of such extension. For example, wrist pads are available to place in front of a keyboard to elevate the wrists and thereby change the angle of the hands with respect to the keyboard. Such wrist pads do not however assist the user when the user has to move his or her hands from side-to-side on the keyboard. In particular, if a person has weak muscles or the like, the person may be unable to move freely about the keyboard. Thus, additional assistance for using keyboards and for performing other tasks requiring arm and hand extension is desirable.

SUMMARY OF THE INVENTION

The present invention provides a free floating support system which is designed to support the arms and hands during prolonged tasks which require the arms and hands to be extended. The system allows freedom of movement over the entire keyboard while providing full support for the arms and hands. The system is ideal for computer keyboards, typewriters, calculators, and horizontally disposed musical instruments (e.g., pianos and electronic keyboards). In addition, the system provides support while performing tedious assembly work, as well as while doing needlework, sewing, painting, and the like.

One aspect of the present invention is a system for supporting a hand of a user when performing manual tasks above a work surface. The system comprises a horizontally disposed guide rail supported a predetermined distance above the working surface. At least one roller is positioned on the guide rail. The roller provides horizontal movement along the guide rail and provides arcuate movement about the guide rail. A cradle is suspended from the roller. The cradle is sized to support a portion of a user's hand, wrist or lower arm above the surface. The cradle permits horizontal movement of the user's hand parallel to the guide rail and permits arcuate movement of the user's hand around the guide rail. Preferably, the guide rail is a round rod.

Another aspect of the present invention is a system for supporting the hands of a user above a work surface such that the user can freely move the hands with respect to the work surface. The system comprises a first end support and a second end support positionable on the work surface. A guide rail is horizontally disposed between the first end support and the second end support. A first pair of rollers and a second pair of rollers are positioned on top of the guide rail for horizontal movement thereon. A first cradle is suspended from the first pair of rollers beneath the guide rail. The first cradle is positioned to support the user's left hand above the work surface. The first cradle moves horizontally with horizontal movement of the first pair of rollers. The first cradle moves arcuately with respect to the guide rail. A second cradle is suspended from the second pair of rollers beneath the guide rail. The second cradle is positioned to support the user's right hand above the work surface. The second cradle moves horizontally with horizontal movement of the second pair of rollers. The second cradle moves arcuately with respect to the guide rail. Preferably, the rail is round, and the rollers roll along the length of the rail and slide around the periphery of the rail. Also preferably, the position of the cradle above the work surface is adjustable.

Another aspect of the present invention is a system which supports the hands of a user above a work surface. The system comprises a first support and a second support positionable on the work surface. A horizontal guide rail is supported at respective first and second ends by the first and second supports. The guide rail has an outer periphery. A first pair of rollers and a second pair of rollers are positioned on top of the guide rail. The rollers move along the top of the guide rail and slide about the periphery of the guide rail. A first cradle is suspended from the first pair of rollers and a second cradle is suspended from the second pair of rollers. The first and second cradles move longitudinally below the guide rail and move arcuately about the guide rail. Preferably, the first cradle and the second cradle are suspended from the first and second pairs of rollers via respective first and second pairs of chains. Also preferably, the system includes an adjustable linkage (e.g., a turnbuckle) to adjust the distance by which the cradles are suspended below the guide rail. In particularly preferred embodiments, the cradle comprises a generally arcuate section of flexible material sized to generally conform with the wrist of a user.

BRIEF DESCRIPTION OF THE DRAWINGS

The present invention will be described below in connection with the accompanying drawing figures in which:

FIGS. 4A, 4B and 4C illustrate cross-sectional views of the overhead rail showing the placement of a trolley wheel on the rod so that the trolley wheel can roll on the rod for left-to-right movement (as viewed in FIG. 3) as well as pivot on the rod to provide front-to-back swinging movement.

DETAILED DESCRIPTION OF THE PREFERRED EMBODIMENT

As illustrated in FIGS. 1–4, the wrist support system in accordance with the present invention comprises of two vertical end supports 2, 3 at each end of a horizontally disposed tracking rod or overhead rail 1. In the illustrated embodiment, the tracking rod 1 comprises a standard plated steel rod, or the like, to provide a substantially non-bending span between the two end supports 2, 3. For example, the rod 1 may advantageously be ⅜ inch in diameter. The rod 1 is preferably threaded at each end. The rod 1 is fastened at each end by two nuts 4, 5, and 6, 7, respectively, with one nut being on each side of the respective tops of the end supports 2, 3.

Figure 1:
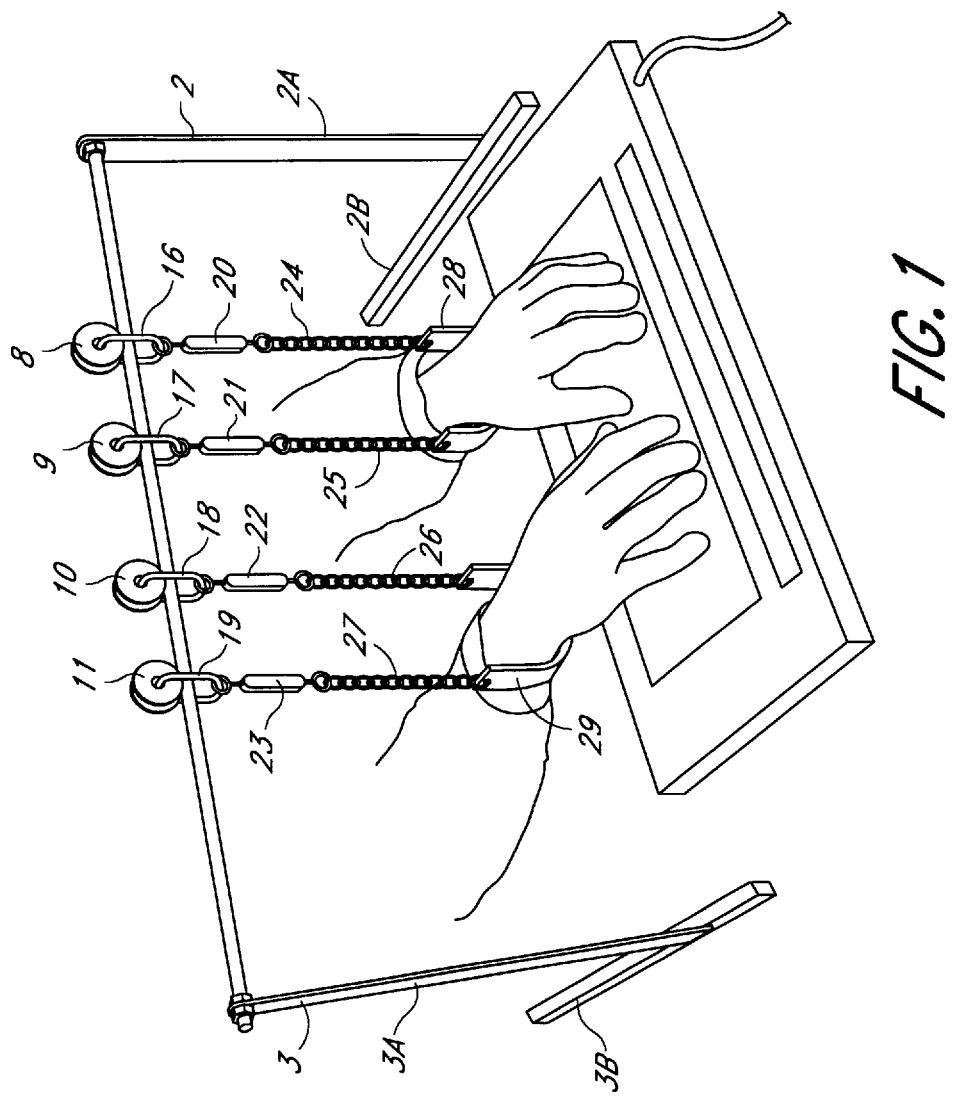
FIG. 1 illustrates a perspective view of the present invention when being used to support a person's arms and hands over a keyboard.
Figure 2:
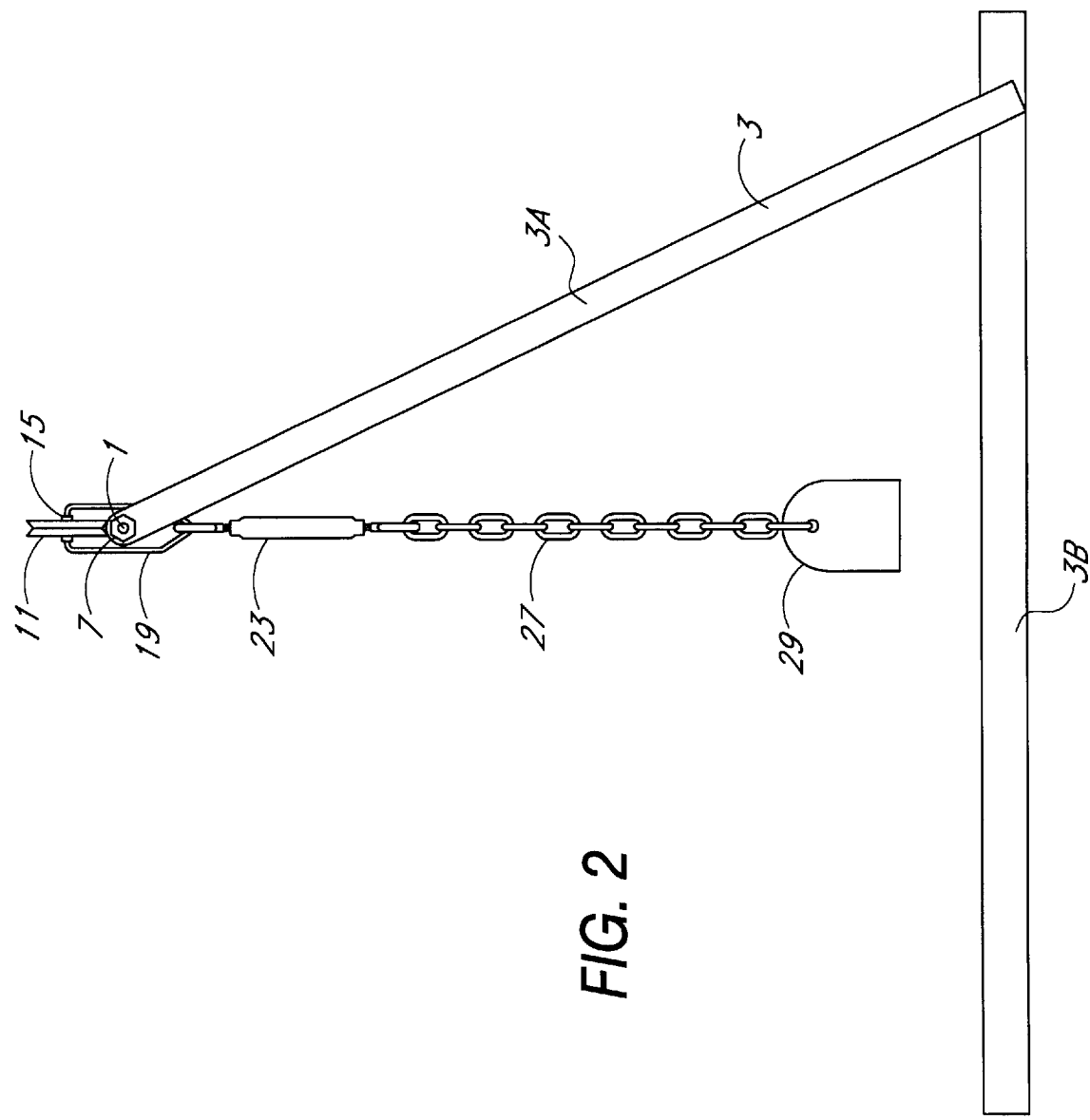
FIG. 2 illustrates a side elevational view of the present invention showing one of the side supports and illustrating the suspension of the wrist cradle beneath the overhead rail.
Figure 3:
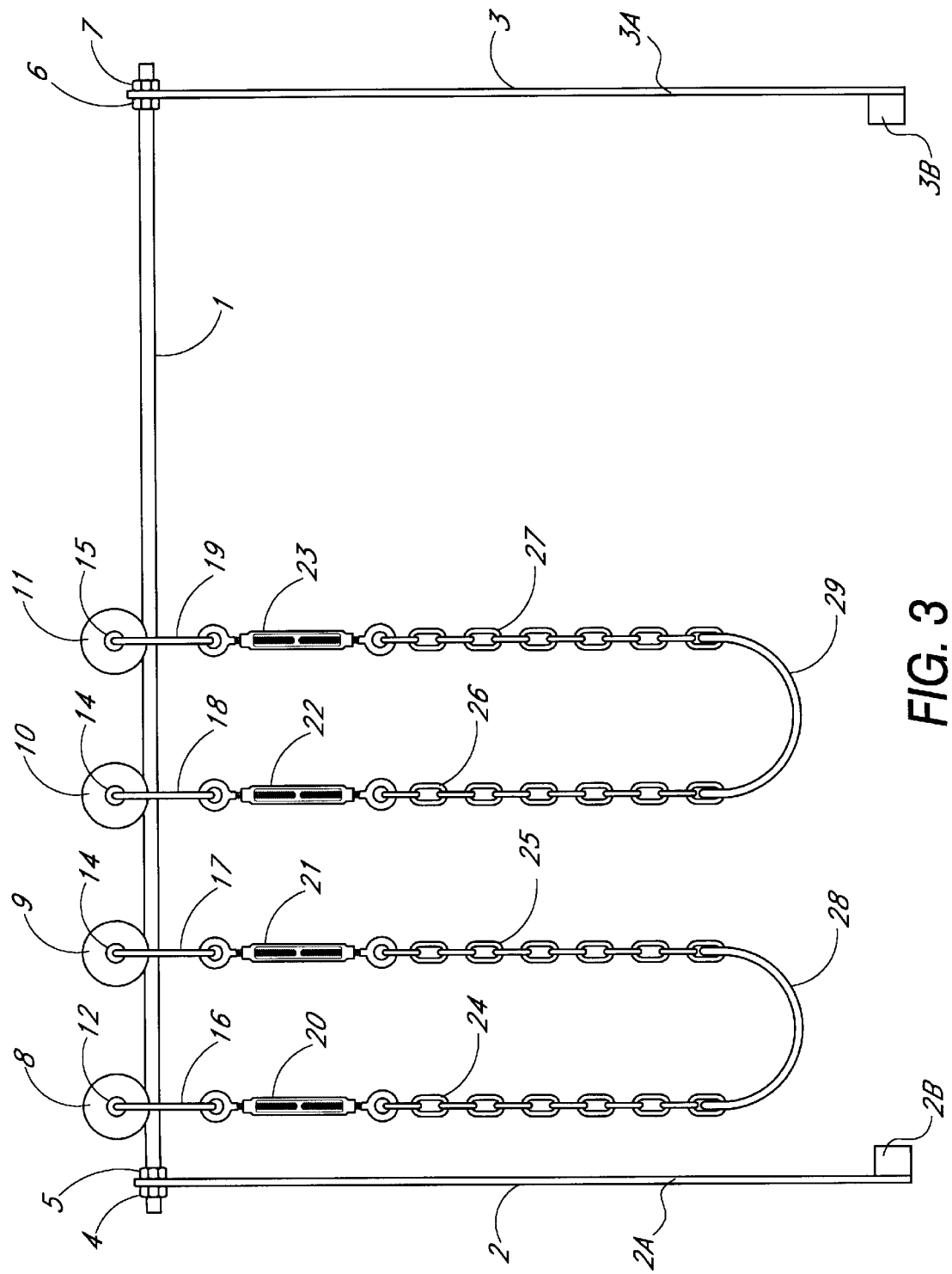
FIG. 3 illustrates a plan view of the present invention showing the overhead rail in more detail and showing the trolley wheels which provide free left-to-right and front-to-back swinging movement of the wrist cradles.

In the preferred embodiment, the end supports have respective first portions 2A, 3A which are positioned at an angle with respect to vertical, and the bottoms of the end supports are directed away from the user (see FIG. 1). The end supports have respective second portions 2B, 3B, which provide stable horizontal platforms for the for the first portions 2A, 3A when the system is positioned on a desk or the like. As illustrated in FIG. 2, the tracking rod 1 is positioned substantially over the centers of the second portions 2B, 3B so that the system is very stable and does not rock during use. Preferably, the second portions 2B, 3B include cushioned pads (not shown) or the like to inhibit sliding of the second portions 2B, 3B on a desktop or other working surface.

The end supports 2, 3 are spaced apart by a distance slightly less than the length of the tracking rod 1 (i.e., by the length of the tracking rod 1 less the lengths of the two threaded ends extending through and beyond the end supports 2, 3). The length of the tracking rod 1 is selected so that the end supports 2, 3 are positioned outside the working area. For example, when the system is used with a conventional computer keyboard having a width of approximately 18 inches, the tracking rod 1 advantageously has a length of 24–30 inches to accommodate the full width of the keyboard as well as a mouse pad, if desired. For packaging purposes, the tracking rod 1 can be provided in two sections (not shown) with one section having an outside threaded portion (not shown) and the other section having a tapped threaded portion.

The tracking rod I supports four grooved wheels 8, 9, 10, 11 which roll on the top side of the tracking rod 1 and thus roll along a straight line substantially parallel to a desktop or other surface on which the system is positioned. The center of each of the grooved wheels 8, 9, 10, 11 includes a sleeve bearing 12, 13, 14, 15. Each sleeve bearing 12, 13, 14, 15 has a hole through its respective center. A respective wire loop 16, 17, 18, 19 passes through the hole in each of the four sleeve bearings 12, 13, 14, 15. Each of the four wire loops 16, 17, 18, 19 straddles and extends below the tracking rod 1, preferably without touching the tracking rod 1, or at least not applying significant pressure on the tracking rod 1 so as to avoid significant frictional contact.

Below the tracking rod, each of the four loops 16, 17, 18, 19 has a respective turnbuckle 20, 21, 22, 23 attached to it such that each turnbuckle is disposed in a generally vertical position below the tracking rod 1 when the system is not in use. A respective chain 24, 25, 26, 27 is attached to the lower end of each of the four turnbuckles 20, 21, 22, 23. The four chains 24, 25, 26, 27 are paired, and each pair of chains 24, 25 and 26, 27 is attached to a respective wrist cradle 28, 29. In particular, the chains 24, 25 support the left wrist cradle 28, and the chains 26, 27 support the right wrist cradle 29. Together, the chains 24, 25, 26, 27 and the turnbuckles 20, 21, 22, 23 permit the wrist cradles 28, 29 to be positioned at any distance below the tracking rod 1 to accommodate different working environments and different personal preferences. For example, links can be removed from or added to the chains for gross adjustment, and the turnbuckle rotated for fine adjustment. It should be understood of course that other suspension devices, such as, for example, string, line or wire, can be used to support the wrist cradles 28, 29.

The wrist cradles 28, 29 may be of any suitable material which provides a reasonable range of flexibility to accommodate different sizes of wrists without being too flexible such that the wrist cradles wrap around the wrists and bind the wrists. For example, in a prototypical embodiment, an arcuate portion of a large diameter automotive rubber hose was found to provide adequate flexibility and support. It is anticipated that many plastic materials will be suitable for the wrist cradles.

The grooved wheels 8, 9, 10, 11 greatly reduce friction and allow omnidirectional motion of the wrist cradles 28, 29. When the wrist cradles 28, 29 are moved from left to right and from right to left horizontally (as viewed by the user in FIG. 1 or in FIG. 3), the wheels 8, 9, 10, 11 roll along the top of the tracking rod 1 along a generally horizontal line. Absent movement by the user, the wrist cradles 28, 29 hang directly below the tracking rod 1 as illustrated by the position of the loop 16, 17, 18, 19 in FIG. 4A. When the wrist cradles 28, 29 are moved toward the user and away from the user (FIG. 1), the wheels 8, 9, 10, 11 pivot around the circumference of the tracking rod 1 as indicated in FIGS. 4B and 4C (i.e., the wheels 8, 9, 10, 11 move arcuately about the tracking rod 1). By using flanged wheels 8, 9, 10, 11, as illustrated in FIGS. 4A–4C, the frictional contact with the tracking rod 1 is very low so that the wheels 8, 9, 10, 11 freely pivot on the tracking rod 1. The wheels readily roll and pivot simultaneously so that the cradles can move left or right at the same time as the cradles move forward or backward. Thus, for example, a user can readily move his or her hand from a key at the left end of the lowest row of the keyboard to a key at the right end of the highest row of the keyboard in one easy movement. In the illustrated embodiment, the wheels 8 and 9 are not coupled and may move independently with respect to each other. Similarly, the wheels 10 and 11 are not coupled and may move independently with respect to each other. In alternative embodiments, the wheels 8 and 9 may be coupled together and the wheels 10 and 11 may be coupled together so that a substantially constant spacing is maintained between the wheels in each pair of wheels.

When using a conventional keyboard having a sloped key layout, it is anticipated that the cradles 28, 29 will be positioned over the keyboard such that the fingers of a user's hand will be generally proximate to the lower row of keys on the keyboard. Then, as the user moves the cradles way from the user's body, the cradles will swing upward so that the user's fingers move up the slope of the keyboard. The four turnbuckles 20, 21, 22, 23 are readily adjusted to change the arc length of the swing of the wrist cradles to compensate for differing keyboard slopes.

The present system provides a natural resting position for the user's wrists and hands. Thus, for example, when using a computer keyboard in conjunction with a mouse, the present system assists the user in returning from a mouse operation to a keyboard without having to look at the keyboard to determine correct hand placement. Thus, the user can continue to watch the screen when transitioning between the two operations.

It can be readily seen from the foregoing that when the free floating support system in accordance with the present invention is used with keyboards, typewriters, data entry devices, musical instruments, and the like, or is used to assist in the performance of tedious assembly work, the system will greatly reduce stresses and strains to the wrists and arms. The present invention is particularly advantageous for a person having weak muscles such that the person cannot readily support his or her hands above a keyboard or other work surface. The wrist cradles provide the necessary support so that the person's remaining muscular capabilities can be applied to the manipulation of the keyboard or to any other task rather than to the effort of supporting the wrists and hands.

While preferred embodiments of this invention have been disclosed herein, those skilled in the art will appreciate that changes and modifications may be made therein without departing from the spirit and scope of the invention as defined in the appended claims.

What is claimed is:

1. A system for supporting a hand of a user when performing manual tasks above a work surface, comprising:

a horizontally disposed guide rail supported a predetermined distance above the work surface, said guide rail having an outer periphery, at least a portion of said outer periphery being arcuate;

at least one roller positioned on said guide rail in contact with said arcuate portion of said outer peripher, said roller providing horizontal movement along said guide rail and providing arcuate movement of said roller about said guide rail; and a cradle suspended from said roller, said cradle sized to support a portion of a user's hand, wrist or lower arm above said work surface, said roller permitting horizontal movement of said cradle and the user's hand parallel to said guide rail and permitting arcuate movement of said cradle and the user's hand around said guide rail.

2. The system as defined in claim 1, wherein said outer periphery of said guide rail is round and said roller slips around the circumference of said guide rail.

3. The system as defined in claim 1, wherein said roller has a flanged peripheral portion and said flanged peripheral portion of said roller engages said arcuate portion of said periphery of said guide rail.

4. The system as defined in claim 1, wherein said work surface is a computer keyboard.

5. The system as defined in claim 1, wherein the position of said cradle above the work surface is adjustable.

6. A system for supporting the hands of a user above a work surface such that the user can freely move the hands with respect to the work surface, said system comprising:

a first end support and a second end support positionable on the work surface;

a guide rail horizontally disposed between said first end support and said second end support, said guide rail having an outer periphery, at least a top portion of said outer periphery being arcuate;

a first pair of rollers and a second pair of rollers positioned on said top portion of said guide rail for horizontal movement thereon and for arcuate movement about said guide rail;

a first cradle suspended from said first pair of rollers beneath said guide rail, said first cradle positioned to support the user's left hand above the work surface, said first cradle moving horizontally with horizontal movement of said first pair of rollers, said first cradle moving arcuately with respect to said guide rail with arcuate movement of said first pair of rollers about said guide rail; and a second cradle suspended from said second pair of rollers beneath said guide rail, said second cradle positioned to support the user's right hand above the work surface, said second cradle moving horizontally with horizontal movement of said second pair of rollers, said second cradle moving arcuately with respect to said guide rail with arcuate movement of said second pair of rollers about said guide rail.

7. The system as defined in claim 6, wherein said guide rail is round and wherein said rollers roll along the length of said guide rail and slide around the periphery of said guide rail.

8. The system as defined in claim 6, wherein the position of said cradle above said work surface is adjustable.

9. A system which supports the hands of a user above a work surface, comprising:

a first support and a second support positionable on said work surface;

a horizontal guide rail supported at respective first and second ends by said first and second supports, said guide rail having an outer periphery, at least a portion of said outer periphery being arcuate;

a first pair of rollers and a second pair of rollers positioned on top of said guide rail in contact with said arcuate portion of said periphery of said guide rail, said rollers moveable along the top of said guide rail and slidable about the arcuate portion of said periphery of said guide rail; and a first cradle suspended from said first pair of rollers and a second cradle suspended from said second pair of rollers, said first and second cradles moveable longitudinally below said guide rail and arcuately about said guide rail.

10. The system as defined in claim 9, wherein said first cradle and said second cradle are suspended from said first and second pairs of rollers via respective first and second pairs of chains.

11. The system as defined in claim 9, further including an adjustable linkage to adjust the distance by which said cradles are suspended below said guide rail.

12. The system as defined in claim 11, wherein said adjustable linkage comprises a turnbuckle.

13. The system as defined in claim 9, wherein each cradle comprises a generally arcuate section of flexible material sized to generally conform with the wrist of a user.

14. A system for supporting a hand of a user when performing manual tasks above a computer keyboard, comprising:

a horizontally disposed guide rail supported a predetermined distance above the computer keyboard;

at least one roller positioned on said guide rail, said roller providing horizontal movement along said guide rail and providing arcuate movement about said guide rail; and a cradle suspended from said roller, said cradle sized to support a portion of a user's hand, wrist or lower arm above said computer keyboard, said cradle permitting horizontal movement of the user's hand parallel to said guide rail and permitting arcuate movement of the user's hand around said guide rail.

* * * * *

UNITED STATES PATENT AND TRADEMARK OFFICE
CERTIFICATE OF CORRECTION

PATENT NO. : 5,876,362
DATED : March 2, 1999
INVENTOR(S) : Warren N. Root

It is certified that error appears in the above-identified patent and that said Letters Patent is hereby corrected as shown below:

In claim 1, at column 5, line 19, change "outer peripher," to --outer periphery,--.

Signed and Sealed this

Seventh Day of December, 1999

Attest:

Q. TODD DICKINSON

*Attesting Officer*     *Acting Commissioner of Patents and Trademarks*